United States Patent [19]

Lee et al.

[11] Patent Number: 4,877,608

[45] Date of Patent: Oct. 31, 1989

[54] PHARMACEUTICAL PLASMA PROTEIN FORMULATIONS IN LOW IONIC STRENGTH MEDIA

[75] Inventors: Ted C. K. Lee, Fairfax; Michael E. Hrinda, Fairfax Station, both of Va.

[73] Assignee: Rorer Pharmaceutical Corporation, Fort Washington, Pa.

[21] Appl. No.: 118,670

[22] Filed: Nov. 9, 1987

[51] Int. Cl.$^4$ .................. A61K 39/395; A61K 35/16; A61K 37/18

[52] U.S. Cl. .................................. 424/85.8; 424/101; 514/2; 514/21; 514/802; 514/8

[58] Field of Search .................. 424/101; 514/21, 802, 514/970, 400; 530/380-384, 389, 392-394, 829-831

[56] References Cited

U.S. PATENT DOCUMENTS

| | | | |
|---|---|---|---|
| Re. 32,011 | 10/1985 | Zimmerman et al. | 530/383 |
| 4,089,944 | 5/1978 | Thomas | 424/101 |
| 4,104,266 | 8/1978 | Wickerhouser | 530/383 |
| 4,188,318 | 2/1980 | Shanbrom | 424/101 |
| 4,321,192 | 3/1982 | Jain | 530/383 |

*Primary Examiner*—Jacqueline M. Stone
*Attorney, Agent, or Firm*—Imre J. Balogh; James A. Nicholson

[57] ABSTRACT

Stable factor VIII and other plasma protein formulations are provided in low ionic strength media which comprises: sodium chloride, potassium chloride or mixtures thereof; lysine hydrochloride; and histidine as the buffering agent.

5 Claims, No Drawings

PHARMACEUTICAL PLASMA PROTEIN FORMULATIONS IN LOW IONIC STRENGTH MEDIA

BACKGROUND OF THE INVENTION

1. Field of the Invention

This invention relates to stable factor VIII formulations. More particularly, high purity factor VIII protein is formulated in low ionic strength media for administration to patients suffering from hemophilia type A.

Antihemophilic factor or factor VIII procoagulation activity protein (hereinafter factor VIII) functions to correct the clotting defect in hemophilic type A plasma. Accordingly, factor VIII preparations are extensively used for the purpose of supplying factor VIII to hemophilic patients.

2. Description of the Prior Art

An important concern associated with the use of factor VIII and other therapeutic agents derived from biological sources is the transmission of diseases, especially viral diseases. Prevalent viral contaminants include hepatitis B virus (HBV), non-A, non-B hepatitis virus (NANBV), and HTLV III/LAV/HIV which cause AIDS. In order to ensure that products produced from biological sources are virus-safe, various methodologies have been proposed for virus inactivation. However, most plasma protein preparations are unstable and require special care to prevent denaturation, alteration and loss of activity during the virus inactivation process. One approach to prevent denaturation and other alteration of plasma proteins utilizes additives during the pasteurization process. Representative examples follow.

U.S. Pat. No. 4,440,679 (Fernandes et al.) describes a method wherein therapeutically active proteins are pasteurized by mixing the protein composition with a pasteurization-stabilizing amount of a polyol prior to pasteurization.

U.S. Pat. No. 4,297,344 (Schwinn et al.) discloses a process for the stabilization against heat of the coagulation factors II, VIII, XIII, antithrombin III and plasminogen in aqueous solution, which comprises adding to the solution both an aminoacid and one or more of a monosaccharide, an oligosaccharide or a sugar alcohol.

U.S. Pat. No. 4,585,654 (Landaburu et al.) pertains to a process of inactivating viruses in plasma protein solutions by heating the same in the presence of a polyol, a surface active agent and a chelating agent.

U.S. Pat. No. 4,446,134 (Naito et al.) is drawn to a virus-inactivating process in which factor VIII is heated in an aqueous solution in the presence of one principal stabilizer of neutral amino acids, monosaccharides, oligosaccharides, and sugar alcohols and an auxiliary stabilizer of salts of hydrocarbon and hydroxyhydrocarbon carboxylic acids.

These processes aim at destroying the potential viral and bacterial infectivity of the preparations while substantially maintaining their desired biological activity. As such, they represent significant steps toward the provision of satisfactory plasma protein products to patients.

In order to be administrable, the plasma protein products need to be formulated with suitable compounds, lyophilized for storage and ready for reconstitution. Before formulating, the additives used during the pasteurization process are removed and their stabilizing/protecting effect is no longer present to prevent loss of activity. Applicants have encountered degradation problems with factor VIII both during lyophilization and upon reconstitution with normal saline solution. To eliminate the effects of residual stabilizing agents and/or other materials used in the prior art during the production or pasteurization, a highly purified factor VIII was used to study degradation occurring during lyophilization and reconstitution such as that produced by the teaching of U.S. Pat. No. 4,361,509. The method there disclosed provides for about one thousand-fold purification of factor VIII obtained from a commercial concentrate using an anti-body column. The subsequent purification step by an Aminohexyl-Sepharose column chromatography further increases purity by 2 to 3-fold resulting in factor VIII activity of over 2,000 units per mg of protein.

Elution of factor VIII from the Aminohexyl-Sepharose is accomplished by the use of calcium chloride solution having a concentration of from 0.25 to 0.5M. This solution, having such high concentration of calcium chloride is not suitable for injection to the patient. More importantly, upon lyophilization, a drastic loss of factor VIII was observed.

To remedy the problems, an isotonic solution was prepared by dialyzing factor VIII contained in said calcium chloride solution against 0.15M sodium chloride, 5 mM calcium chloride and 3 mM histidine at pH 6.8. Upon testing, a drastic loss of factor VIII was again observed.

It has now been discovered that factor VIII as well as other plasma and recombinant proteins, can be formulated with physiologically acceptable compounds for stabilization against loss of activity during lyophilization, storage in the lyophilized state and reconstitution preceding administration to patients.

SUMMARY OF THE INVENTION

In accordance with the present invention plasma and recombinant protein formulations are provided which are stable, and upon reconstitution, are ready for administration into patients. The formulations comprise at least one particular protein as the active ingredient for therapeutic use and a low ionic strength medium. The amount of protein present in a formulation is based on its known activity against the ailments to be treated and will vary from protein to protein, their concentration and state of purity. The low ionic strength medium is an aqueous solution of and comprises:

(a) from about 0.5 mM to about 15 mM sodium chloride or potassium chloride or mixtures thereof and preferably about 1.5 mM sodium chloride;

(b) from about 0.01 mM to about 10 mM and preferably about 0.20 to 2.0 mM lysine hydrocloride; and (c) from about 0.2 mM to about 5 mM and preferably about 0.5 to 1.0 mM histidine as buffer ion.

The pH of the media should be from about 6.0 to about 7.6 and preferably about 7.0.

Optionally, up to about 10% w/v of sugars, such as mannitol, sucrose and maltose, may be added to the formulations of the present invention for lyophilization. The addition of maltose (10%), sucrose (10%) or mannitol (5%) makes the formulated factor VIII solution isotonic.

The formulation is lyophilized and stored in that state. Prior to use it is reconstituted with water to the volume present before lyophilization.

The formulations containing 10 to 500 units of factor VIII per ml of solution have been found effective for the treatment of hemophilia.

DETAILED DESCRIPTION OF THE INVENTION

The present invention encompasses proteinaceous materials and products in the biomedical field intended for use in the human or animal body for biomedical or therapeutic purposes as well as non-therapeutic experimental purposes. Contemplated materials and products include but are not limited to:

Blood fractions such as antihemophilic factor (Smith, J. K and Bidwell, E. (1979) Clinics in Haemotol. 8, pp. 184–205);

Prothrombin complex, i.e., Factors II, VII, IX and X (Chandra, S. and Brummelhuis, H. G. J. (1981) Vox Sang. 41, pp. 259–273);

Protein C. (Steuflo, J. (1976) J. Biol. Chem. 251. pp. 355–363 and Bajaj, S. P. et al. (1983) Prep. Biochem. 13 pp. 191–214); Protein S (DiScipio, R. G., et al. (1977) Biochem. 16, pp. 698–706;

Antithrombin III (Rosenberg, R. D., and Damus, P. S. (1973) J. Biol. Chem. 248, pp. 6490–6505;

Gamma Globulin (Oncley et al. (1949) J. Amer. Chem. Soc. 71, pp. 541–550;

Biological materials and products derived by recombinant DNA techniques and produced in bacteria, fungi, or mammelian cell culture systems (Vane, J. and Cuatrecases, P. (1984), Nature 312, pp. 303–305 and Meniatis, T. et al. (1982), Molecular cloning: A Laboratory Manual, (Old Spring Harbor, N.Y.).

These products and materials are available from various commercial sources or can be produced by using well-known preparative techniques. For example, blood fractions and blood proteins can be obtained from human blood plasma by fractionation according to known techniques such as, for example, the alcohol fractionation of Cohn described in U.S. Pat. No. 2,390,074 and the Journal of the American Chemical Society Vol. 68, p.459 (1946). These methods as well as other techniques are summarized in "The Plasma Proteins", second edition, Vol. III, pp. 548–550, Academic Press, New York, N.Y. (1977).

While the invention is applicable to these and other similar products and materials, it will be described in detail in reference to factor VIII procoagulant activity protein produced according to U.S. Pat. No. 4,361,509. The method therein disclosed is capable of producing highly purified and concentrated factor VIII which is effective in the treatment of hemophilia, having more than two thousand units of factor VIII procoagulant activity per mg of protein. However, the product as obtained by the process is unstable during lyophilization and upon reconstitution. Furthermore, the high calcium ion solution containing the factor is undesirable for administration to the patients. The following examples and tests will further illustrate the invention.

EXAMPLE 1

The rate of factor VIII degradation under isotonic conditions was studied. Factor VIII, obtained by the process of U.S. Pat. No. 4,361,509, in buffered 500 mM calcium chloride solution was dialyzed against 1M sodium chloride, 0.035M calcium chloride and 3 mM histidine at pH 6.8, for salt exchange, and then was lyophilized. Reconstitution of the lyophilized material was made to 0.167M sodium chloride, 5.8 mM calcium chloride, and 3 mM histidine by adding a 6-fold volume of 2.5 mM histidine, at pH 6.8, over the pre-lyophilization volume. The time dependent decay of factor VIII activity was determined by the two stage assay method which is essentially the same as the method described by Newman, J., Johnson, A. J., Karpatkin, S. and Puszkin, S. (1971), Br. J. Haematol. 21. pp. 1–20. The results are shown in Table I.

TABLE I

| Time Dependent Decay of Factor VIII Activity Under Isotonic Conditions | | |
|---|---|---|
| Time (Minutes) | Factor VIII Activity (Total Unit) | % Decay |
| 0 (At reconstitution) | 21 | 0 |
| 15 | 17 | 18 |
| 30 | 14 | 32 |
| 60 | 10 | 52 |

The following examples illustrate the present invention.

EXAMPLE 2

1 kg of frozen human plasma cryoprecipitate was placed in 2.8 kg of 0.055M glycine and 0.038M sodium chloride. The mixture was placed in a 37° C. water bath and agitated under laminar flow of air to form a suspension of the cryoprecipitate. 0.1N acetic acid was added dropwise to the suspension to bring the pH to 6.0±0.1. One hundred grams of Rehsorptar (2% aluminum hydroxide gel, Armour Pharmaceutical Company, Kankakee, Ill.) were added to the mixture to adsorb vitamin K-dependent blood coagulation factors and agitated for 15 to 20 minutes at 35° to 37° C. The suspension was centrifuged at 4,000×g at room temperature for 15 minutes and the supernatant was collected. The Rehsorptar treatment was repeated one more time.

3.113 kg of this solution (18,297 units of Factor VIII), was applied to an affinity column (13.7 cm×22.0 cm, 3.24 ) of monoclonal anti-von Willebrand antibody gel matrix, which was previously prepared by conjugation of 1.2 g of of the antibody per l of Sepharose gel. The column was then washed with 3 column volumes of the Factor VIII buffer. Nineteen percent (3,537 units) of the Factor VIII were not bound to the column. The column was eluted with 0.25M calcium chloride in the Factor VIII buffer. The Factor VIII activity containing portion, 3.556 kg (9,880 units), was collected. The eluted Factor VIII was applied on to an Aminohexyl-Sepharose column (2.5 cm×5.6 cm, Pharmacia) immediately after a five-fold in-line dilution with the AH-Sepharose equilibration buffer (20 mM histidine, 100 mM lysine hydrochloride, pH 6.8). The flow rate was 12 ml per minute.

There was no detectable Factor VIII activity in the solution that passed through the AH-Sepharose column. The column was washed with 209 g of 50 mM calcium chloride in the AH-Sepharose equilibration buffer. A small amount of Factor VIII activity (165 units, 1.7%) was detected in the wash buffer solution collected. The Factor VIII was then eluted from the column with 500 mM calcium chloride in the AH-Sepharose equilibration buffer. The peak fraction of the elution profile contained 6,890 units of Factor VIII in 26.5 g. The eluted Factor VIII was dialized overnight at 4° C. against the buffer solution composed of 1M sodium chloride, 5 mM calcium chloride, 3 mM histidine, 2% mannitol, pH 7.0. The dialized Factor VIII had 266 μ/ml and 23 g.

The Factor VIII solution was redialyzed at 4° C. against a low ionic strength formulation buffer composed of 1.5 mM sodium chloride, 0.2 mM lysine hydrochloride, 0.2 mM histidine, pH 7.0. The redialyzed Factor VIII solution had 299 units per ml. Maltose was added to make the Factor VIII solution 10% in maltose, which is isotonic, and lyophilized. Reconstitution of the lyophilized material was made to its original volume with water for injection. Reconstitution was immediate.

Activity of Factor VIII was measured by the two stage method referred to in Example 1. The results are shown in Table II.

TABLE II

Factor VIII Activity After Reconstitution

| | Time After Reconstitution (hours) | | | | | |
|---|---|---|---|---|---|---|
| | 0 | ½ | 1 | 2 | 3 | 24 |
| Activity (μ/ml) | 234 | 232 | 217 | 224 | 207 | 199 |
| % Recovery | 100 | 99 | 93 | 96 | 88 | 85 |

During the formulation process Factor VIII activity is substantially preserved as illustrated in Table III.

EXAMPLE 3

Factor VIII was isolated from cryoprecipitate as described in Example 2. The isolated Factor VIII was dialyzed at 4° C. against 1M sodium chloride, 3 mM histidine, 5 mM calcium chloride, 2% mannitol, pH 7.0. The dialyzed material, 14.50 g (5,815 units) was formulated by redialysis at 4° C. against 1.5 mM sodium chloride, 0.2 mM lysine hydrochloride, 1.0 mM histidine, and 10% maltose at pH 7.0. The dialyzed material had 5,538 units of Factor VIII activity in 10.65 g. The formulated Factor VIII was sterile filtered through 0.2 μm pore size membrane, and 5,325 units were recovered. The formulated and filtered Factor VIII was lyophilized and reconstituted. All of 5,325 units were recovered.

TABLE III

Factor VIII Activity During Preparation

| Steps | Amount u/ml | (g) | Total U | Yield % |
|---|---|---|---|---|
| Factor VIII in buffered 1 M NaCl | 401 | 14.50 | 5,815 | 100 |
| Factor VIII in low ionic strength buffer | 520* | 10.65* | 5,538 | 95 |
| Post-filtration through a 0.2 μm pore size membrane | 500 | 10.65 | 5,325 | 92 |
| Post-lyophilization and reconstitution | 500 | 10.65 | 5,325 | 92 |

*The activity of the material increased due to the small degree of concentration of the solution.

EXAMPLE 4

Factor VIII was isolated from cryoprecipitate as described in Example 2. The isolated Factor VIII was dialyzed at 4° C. against 1M sodium chloride, 3 mM histidine, 5 mM calcium chloride, 2% mannitol, pH 6.0. The dialyzed material, 16.00 g (6,100 units) was formulated by redialysis at 4° C. against 5.0 mM sodium chloride, 3.0 mM lysine hydrocloride and 2.0 mM histidine at pH 6.0. The dialyzed material had 5,700 units of Factor VIII activity in 13.85 g. The formulated Factor VIII was sterile filtered through a 0.2 μm pore size membrane, and 5,450 units were recovered. The formulated and filtered Factor VIII was lyophilized and reconstituted. 5,380 units of Factor VIII were recovered.

EXAMPLE 5

Factor VIII was isolated from cryoprecipitate as described in Example 2. The isolated Factor VIII was dialyzed at 4° C. against 1M sodium chloride, 3 mM histidine, and 5 mM calcium chloride at pH 7.0. The dialyzed material, 15.70 g (5,915 units) was formulated by redialysis at 4° C. against 3.0 mM sodium chloride, 7 mM lysine hydrochloride and 3 mM histidine at pH 6.5. The dialyzed material had 5,550 units of Factor VIII activity in 12.10 g. The formulated Factor VIII was sterile filtered through a 0.2 μm pore size membrane, and 5,380 units were recovered. The formulated and filtered Factor VIII was lyophilized and reconstituted. 5,400 units of Factor VIII were recovered.

It should be understood by those skilled in the art that various modifications may be made in the present invention without departing from the spirit and scope thereof as described in the specification and defined in the appended claims.

What is claimed is:

1. A stable injectable, pharmaceutical plasma protein formulation comprising in an aqueous solution:
   a therapeutically effective amount of a plasma protein selected from the group consisting of Factors II, VII, VIII, IX, X, Protein C, Antithrombin III, and gamma globulin;
   from about 0.5 mM to about 15 mM sodium chloride, potassium chloride, or mixtures thereof;
   from about 0.01 mM to about 10 mM lysine hydrochloride; and
   from about 0.2 mM to about 5.0 mM histidine;
   said aqueous solution having a pH of from about 6.0 to about 7.6.

2. A stable injectable, pharmaceutical plasma protein formulation comprising in an aqueous solution:
   a therapeutically effective amount of a plasma protein selected from the group consisting of Factors II, VII, VIII, IX, X, Protein C, Antithrombin III, and gamma globulin;
   about 1.5 mM sodium chloride, potassium chloride or mixtures thereof;
   from about 0.2 mM to about 2.0 mM lysine hydrochloride; and
   from about 0.5 mM to about 1.0 mM histidine;
   said aqueous solution having a pH of from about 6.0 to about 7.6.

3. The formulation of claim 2 wherein said Factor VIII has a concentration of from about 10 to about 500 units per ml of said aqueous solution.

4. A stable injectable, pharmaceutical plasma protein formulation in lyophilized form comprising upon reconstitution with pyrogen-free water:
   a therapeutically effective amount of a plasma protein selected from the group consisting of Factors II, VII, VIII, IX, X, Protein C, Antithrombin III, and gamma globulin;
   from about 0.5 mM to about 15 mM sodium chloride, potassium chloride, or mixtures thereof;
   from about 0.01 mM to about 10 mM lysine hydrochloride; and
   from about 0.2 mM to about 5.0 mM histidine;
   said formulation having a pH of from about 6.0 to about 7.6.

5. A stable injectable, pharmaceutical plasma protein formulation in lyophilized state comprising upon reconstitution with pyrogen-free water:
  a therapeutically effective amount of a plasma protein selected from the group consisting of Factors II, VII, VIII, IX, X, Protein C, Antithrombin III and gamma globulin;
  about 1.5M sodium chloride, potassium chloride, or mixtures thereof;
  from about 0.2 mM to about 2.0 mM lysine hydrochloride; and
  from about 0.5 mM to about 1.0 mM histidine;
  said formulation having a pH of from about 6.0 to about 7.6.

* * * * *

UNITED STATES PATENT AND TRADEMARK OFFICE
CERTIFICATE OF CORRECTION

PATENT NO. : 4,877,608

DATED : October 31, 1989

INVENTOR(S) : Ted C.K. Lee and Michael E. Hrinda

It is certified that error appears in the above-identified patent and that said Letters Patent is hereby corrected as shown below:

In Column 4, line 41, the portion reading "3.24)" should read --3.24$\ell$--;

In Column 5, line 2, delete "µ" and insert --u--;

In Column 8, line 1, the portion reading "1.5M" should read --1.5mM--.

Signed and Sealed this

Eleventh Day of December, 1990

Attest:

HARRY F. MANBECK, JR.

Attesting Officer

Commissioner of Patents and Trademarks